(12) United States Patent
Liu et al.

(10) Patent No.: US 9,491,553 B2
(45) Date of Patent: Nov. 8, 2016

(54) METHOD OF AUDIO SIGNAL PROCESSING AND HEARING AID SYSTEM FOR IMPLEMENTING THE SAME

(71) Applicants: Ching-Feng Liu, Kaohsiung (TW); Hsiao-Han Chen, Tainan (TW)

(72) Inventors: Ching-Feng Liu, Kaohsiung (TW); Hsiao-Han Chen, Tainan (TW)

( * ) Notice: Subject to any disclaimer, the term of this patent is extended or adjusted under 35 U.S.C. 154(b) by 0 days.

(21) Appl. No.: 14/464,501

(22) Filed: Aug. 20, 2014

(65) Prior Publication Data

US 2015/0172830 A1 Jun. 18, 2015

(30) Foreign Application Priority Data

Dec. 18, 2013 (TW) .............................. 102146946 A

(51) Int. Cl.
| | |
|---|---|
| *H04R 25/00* | (2006.01) |
| *H04N 7/18* | (2006.01) |
| *A61B 5/117* | (2016.01) |
| *G02C 11/06* | (2006.01) |
| *G10L 15/25* | (2013.01) |
| *G06K 9/00* | (2006.01) |
| *G10L 21/0216* | (2013.01) |

(52) U.S. Cl.
CPC ............. *H04R 25/40* (2013.01); *A61B 5/1176* (2013.01); *G02C 11/06* (2013.01); *G10L 15/25* (2013.01); *H04N 7/183* (2013.01); *H04R 25/407* (2013.01); *H04R 25/554* (2013.01); *G06K 9/00221* (2013.01); *G10L 2021/02166* (2013.01); *H04R 25/558* (2013.01); *H04R 2225/61* (2013.01); *H04R 2430/20* (2013.01)

(58) Field of Classification Search
USPC ......................................... 381/71.1
See application file for complete search history.

(56) References Cited

U.S. PATENT DOCUMENTS

| | | | |
|---|---|---|---|
| 7,760,898 B2 * | 7/2010 | Howell ................... | G02C 5/001 381/322 |
| 2002/0135618 A1 * | 9/2002 | Maes .................... | G06F 3/0481 715/767 |
| 2007/0248238 A1 * | 10/2007 | Abreu .................... | G02C 3/003 381/381 |
| 2012/0242860 A1 * | 9/2012 | Noren ............... | G06F 17/30758 348/231.4 |

\* cited by examiner

*Primary Examiner* — Amir Etesam
(74) *Attorney, Agent, or Firm* — Muncy, Geissler, Olds & Lowe, P.C.

(57) ABSTRACT

In a method of audio signal processing, a hearing aid system is configured to: collect sound information of a surrounding environment of the hearing aid system; capture an image of the surrounding environment of the hearing aid system; perform a directional signal processing operation on the sound information so as to generate an output audio signal; the output audio signal containing an extracted voice signal that comes from an area corresponding to a location of a target object in the image; and output the output audio signal.

30 Claims, 5 Drawing Sheets

METHOD OF AUDIO SIGNAL PROCESSING AND HEARING AID SYSTEM FOR IMPLEMENTING THE SAME

CROSS-REFERENCE TO RELATED APPLICATION

This application claims priority of Taiwanese Application No. 102146946, filed on Dec. 18, 2013.

FIELD OF THE INVENTION

The invention relates to a method of audio signal processing and a hearing aid system, more particularly to a method of audio signal processing and a hearing aid system that utilizes both image and sound information to press sound.

BACKGROUND OF THE INVENTION

The term "cocktail party effect" refers to a person's hearing ability to selectively focus on a particular voice while "filtering out" other voices, even in a normally noisy cocktail party. This is the result of a normal person's auditory system being able to "localize" a sound source and extract sound information from the location of the sound source. That is, even in a noisy environment, one may be able to have a conversation with a target speaker by simply focusing on him/her.

However, people with hearing impairment may not have the ability to localize the sound source. This is due to a "threshold of hearing" of a person with impaired hearing ability being higher than that of a normal person. In addition, people with only one normal ear may not have such an ability as well.

Conventional hearing aid systems are provided for helping a person with impaired hearing ability to localize a sound source. For example, a conventional hearing aid system may be configured to extract sound information from a front direction of a user, and process the extracted sound information to increase a signal-to-noise ratio (SNR). As a result, the user is able to listen clearly to the voice of a speaker in front of him/her even in a noisy environment.

Nonetheless, in cases where multiple people are present in front of the user, the conventional hearing aid system is unable to specify which one is (or ones are) the user's target speaker.

SUMMARY OF THE INVENTION

Therefore, an object of the present invention is to provide a method of audio signal processing for helping a user to focus on a target speaker when a plurality of speakers are present.

Accordingly, a method of audio signal processing of this invention is to be implemented by a hearing aid system that includes an image capturing module, a sound pickup module, and a processor. The method comprises:

(a) collecting, using the sound pickup module, sound information of a surrounding environment of the hearing aid system;

(b) capturing, using the image capturing module, an image of the surrounding environment of the hearing aid system;

(c) using the processor to perform a directional signal processing operation on the sound information collected by the sound pickup module so as to generate an output audio signal, the output audio signal containing an extracted voice signal that comes from an area corresponding to a location of a target object in the image captured by the image capturing module; and (d) outputting the output audio signal.

Another object of the present invention is to provide a hearing aid system configured to execute the above-mentioned method.

Accordingly, a hearing aid system of this invention comprises a sound pickup module, an image capturing module, a processor, and an audio output device.

The sound pickup module is for collecting sound information of a surrounding environment of the hearing aid system.

The image capturing module is for capturing an image of the surrounding environment of the hearing aid system.

The processor is coupled to the sound pickup module and the image capturing module, and includes a sound processing module that performs a directional signal processing operation on the sound information collected by the sound pickup module so as to generate an output audio signal. The output audio signal contains an extracted voice signal that comes from an area corresponding to a location of a target object in the image captured by the image capturing module.

The audio output device is coupled to the processor for outputting the output audio signal.

BRIEF DESCRIPTION OF THE DRAWINGS

Other features and advantages of the present invention will become apparent in the following detailed description of the embodiments with reference to the accompanying drawings, of which.

DETAILED DESCRIPTION OF THE EMBODIMENTS

Figure 1:
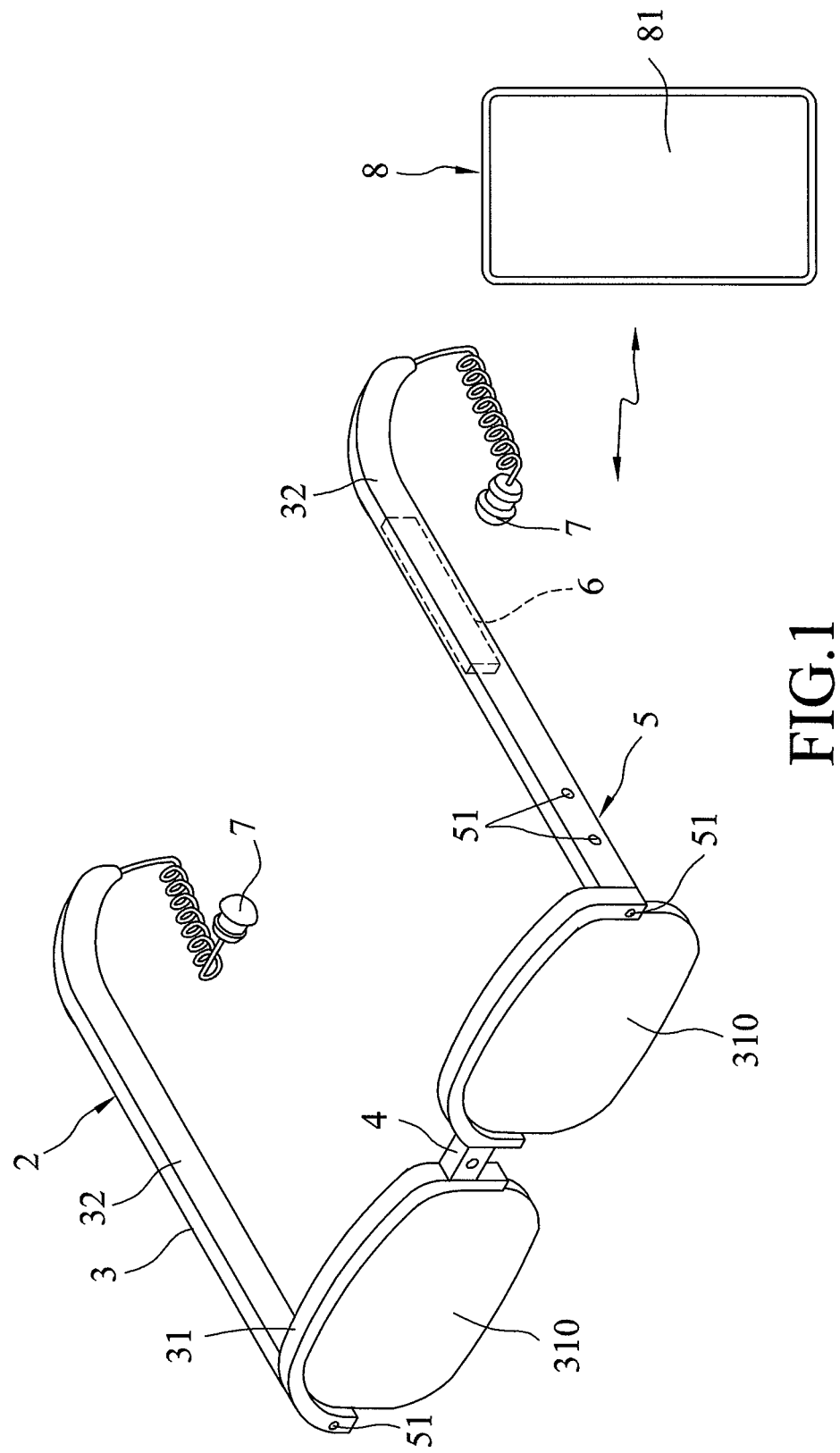
FIG. 1 is a perspective view of an embodiment of a hearing aid system, according to the present invention.

FIG. 1 illustrates an embodiment of a hearing aid system 2 according to this invention. In this embodiment, the hearing aid system 2 is designed to include a wearable accessory 3 that may be worn by a user.

The hearing aid system 2 comprises electronic components including an image capturing module 4, a sound pickup module 5, a processor 6 and an audio output device 7. In this embodiment, electronic components of the hearing aid system 2 are mounted on the wearable accessory 3. The wearable accessory 3 includes a front frame part 31 on which the image capturing module 4 is disposed, and left and right side supports 32 respectively connected to left and right sides of the front frame part 31. In this embodiment, the wearable accessory 3 is an eyeglass frame having a lens frame serving as the front frame part 31, and a pair of temples serving as the left and right side supports 32. The front frame part 31 may hold lenses 310.

Figure 4:
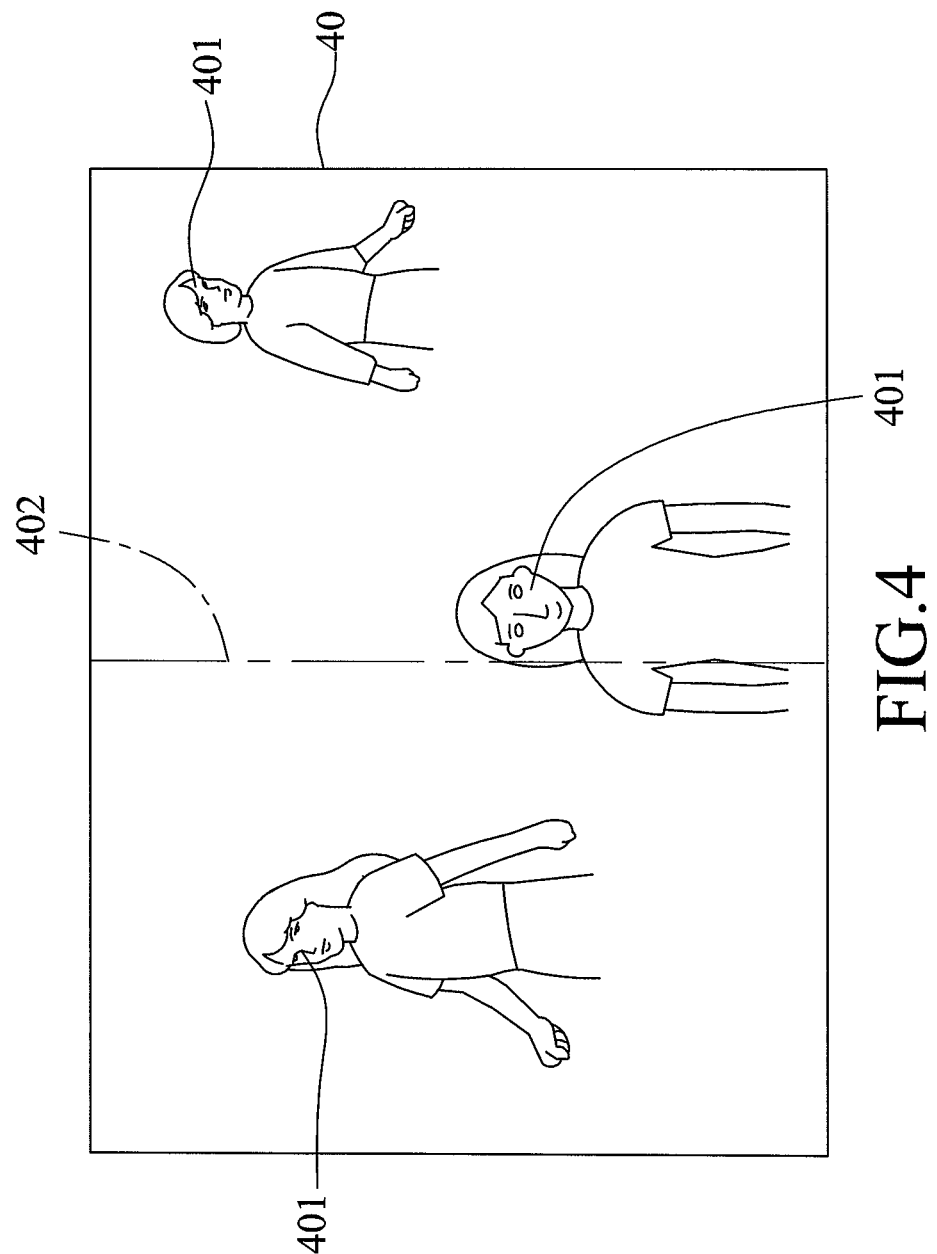
FIG. 4 illustrates an exemplary image captured by the hearing aid system.

The image capturing module 4 is for capturing an image 40 of a surrounding environment of the hearing aid system 2 (See FIG. 4). In this embodiment, the image capturing module 4 is a camera that is mounted between the lenses 310 and that is configured to capture a plurality of the images 40 successively. In this embodiment, the sound pickup module 5 is a microphone array that includes a plurality of microphones 51. The microphones 51 are disposed on the front frame part 31 and the left and right side supports 32 for collecting sound information of the surrounding environment of the hearing aid system 2.

It is noted that the microphones 51 with various directionalities may be utilized in this embodiment, such as omnidirectional, unidirectional, or a combination thereof.

The processor 6 is mounted at one of the left and right side supports 32, and is coupled to the image capturing module 4 and the sound pickup module 5. In this embodiment, with reference to FIG. 2, the processor 6 includes an image analysis module 61 and a sound processing module 62.

The image analysis module 61 is configured to identify presence of human face objects 401 (see FIG. 4) in the image 40 captured by the image capturing module 4. Furthermore, the image analysis module 61 is configured to determine object information corresponding respectively to the identified human face objects 401, and to determine a likelihood classification for each of the identified human face objects 401 based on the object information corresponding thereto. For each of the identified human face objects 401, the likelihood classification is related to a likelihood of a person corresponding to the identified human face object 401 being a target speaker.

In this embodiment, the object information determined by the image analysis module 61 includes relative depth information and relative orientation information for the corresponding identified human face object 401 relative to the hearing aid system 2. In this embodiment, the relative orientation information indicates an included angle formed between a reference axis in the image 40 and the location of the corresponding identified human face object 401 in the image 40. The reference axis represents an axis of the image capturing module 4 (which is disposed on the front frame part 31 between the lenses 310 as best shown in FIG. 1). In this embodiment, the relative orientation information further indicates an angle by which the corresponding identified human face object 401 is turned in the image 40.

Figure 2:
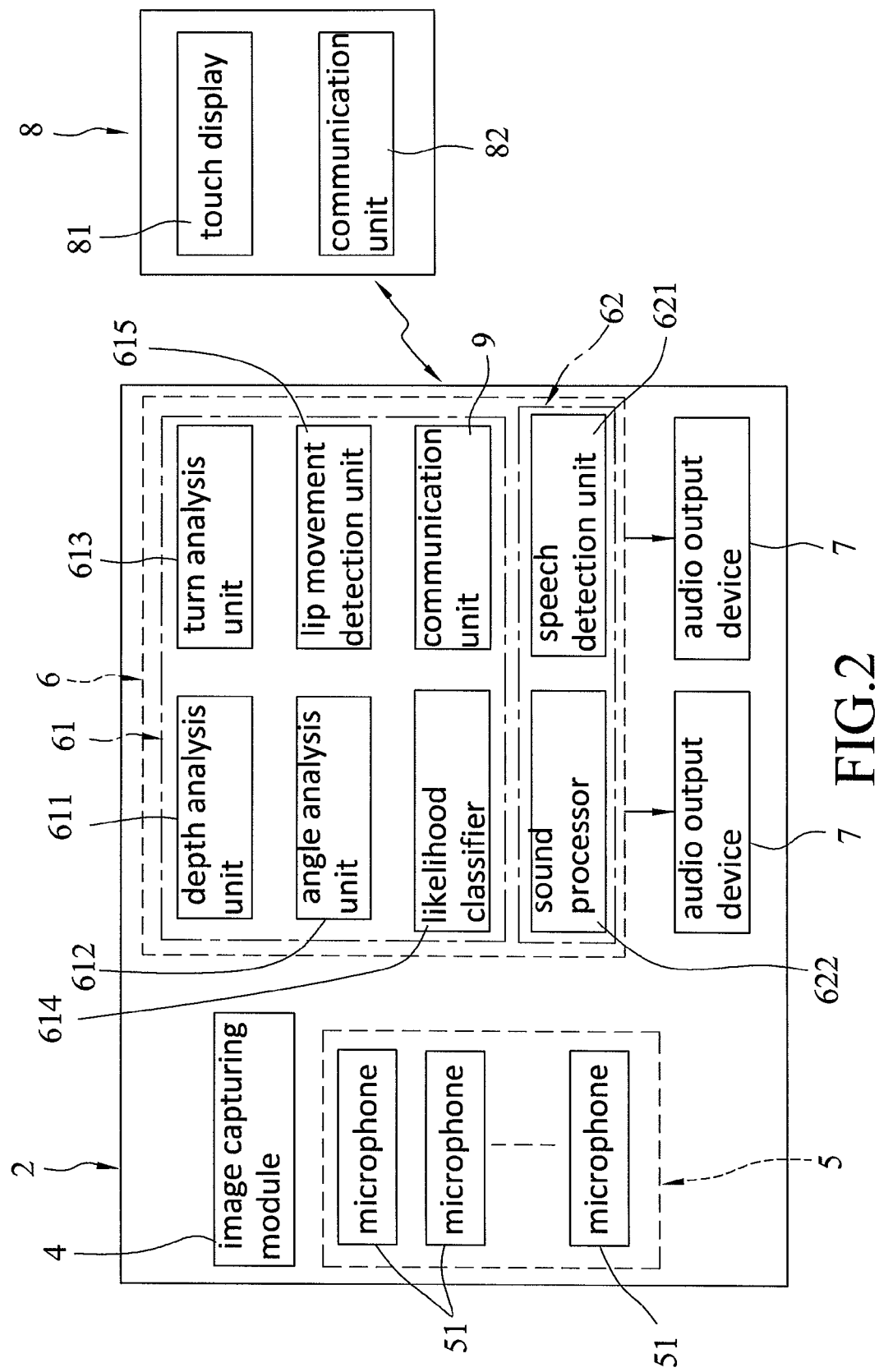
FIG. 2 is a block diagram of the hearing aid system according to the embodiment.

Accordingly, as shown in FIG. 2, the image analysis module 61 includes a depth analysis unit 611, an angle analysis unit 612, a turn analysis unit 613, a likelihood classifier 614, and a lip movement detection unit 615.

The depth analysis unit 611 is for determining a relative depth of each of the identified human face objects 401 in the image 40 relative to the hearing aid system 2. In this embodiment, the depth analysis unit 611 stores a database containing information of a relation between a size of an identified human face object 401 and the relative depth of the identified human face object 401. In use, the depth analysis unit 611 is configured to obtain the size of each of the identified human face objects 401 by, for example, calculating an area of each of the identified human face objects 401 in the image 40. Afterward, the depth analysis unit 611 is configured to determine the relative depth of each of the identified human face objects 401 in the image 40 with reference to the database. It is noted that, other techniques for determining the relative depth may be employed in other embodiments of this invention.

Figure 5:
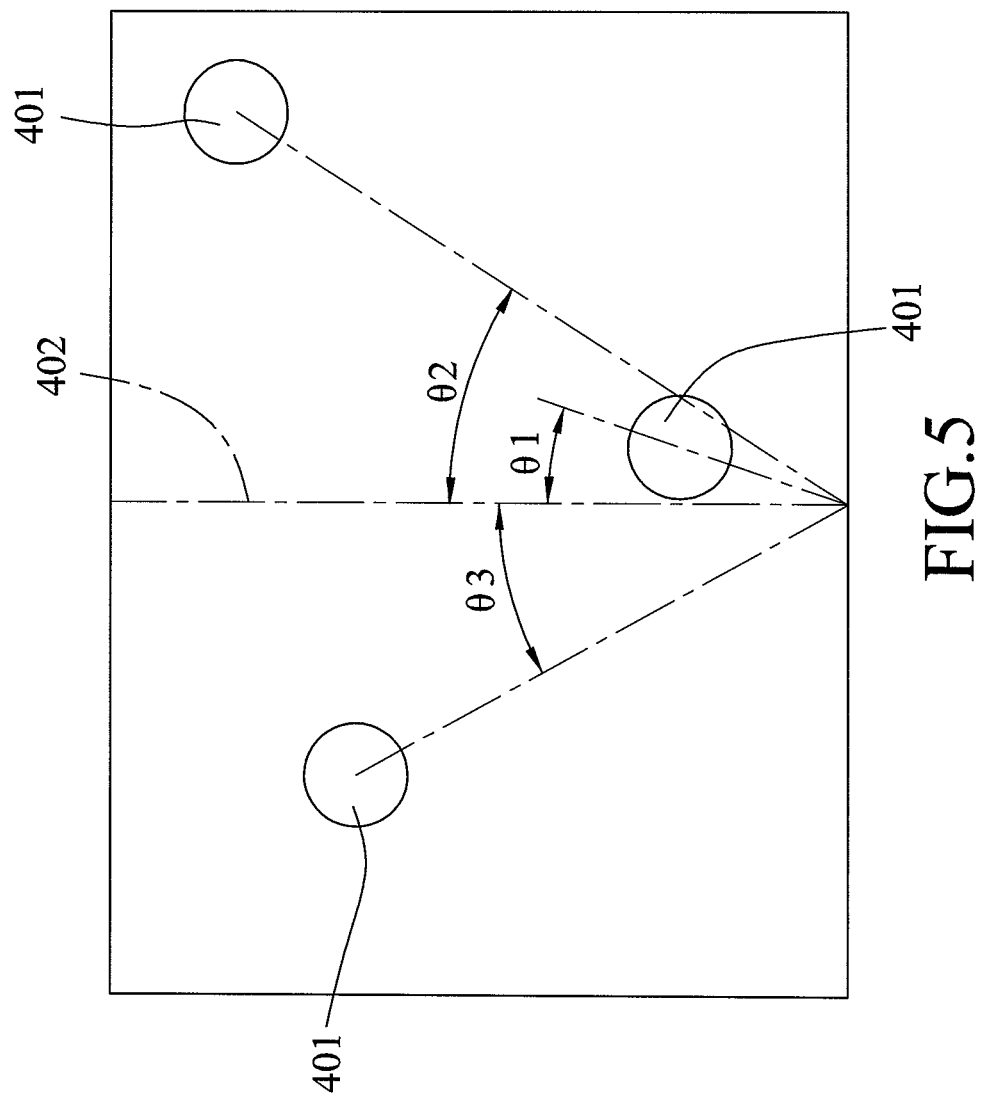
FIG. 5 illustrates included angles between a reference axis in the exemplary image and the locations of a plurality of identified human face objects in the exemplary image, the reference axis representing an axis of the image capturing module of the hearing aid system.

Referring to FIG. 5, the angle analysis unit 612 is for determining included angles each formed between a reference axis 402 in the image 40 and the location of a corresponding one of the identified human face objects 401 in the image 40, the reference axis 402 representing an axis of the image capturing module 4. In this embodiment, since the image capturing module 4 is disposed on the front frame part 31 between the lenses 310, the reference axis 402 may represent a line of sight of a user wearing the wearable accessory 3.

FIG. 5 illustrates three identified human face objects 401, and the respective included angles formed with the reference axis 402 (i.e., $\theta_1$, $\theta_2$ and $\theta_3$). Using the relative depth and the included angle of each of the identified human face objects 401, the image analysis module 61 is capable of obtaining a relative location of each of the identified human face objects 401 with reference to the hearing aid system 2. It is noted that, other techniques for determining the relative locations of the identified human face objects 401 may be employed in other embodiments of this invention.

The turn analysis unit 613 is for determining an angle by which each of the identified human face objects 401 is turned in the image 40. That is, an angle by which a person turns his/her face away from a user wearing the wearable accessory 3.

The likelihood classifier 614 is configured to determine a likelihood classification for each of the identified human face objects 401, based on the object information corresponding thereto, that is, the relative depth information and the relative orientation information.

In this embodiment, different relative depths are pre-assigned with different weights, different relative orientations are pre-assigned with different weights, and the likelihood classification for each of the identified human face objects 401 is determined by the likelihood classifier 614 with reference to the weights corresponding to the relative depth information and the relative orientation information of the respective object information.

As an example, it is known that the distance between individuals who are having a conversation may be related to the relationship between the individuals. Studies on Proxemics categorize personal space of a person into four sections: intimate distance (less than 0.5 meter from the person); personal distance (0.5 to 1.5 meters from the person); social distance (1.5 to 3 meters from the person); and public distance (larger than 3 meters from the person). That is, it is more likely that a person is addressing the user of the hearing aid system 2 when the person is within a closer distance to the user.

Additionally, it is more likely that a person is addressing the user of the hearing aid system 2 when the person is located near the line of sight of the user, and/or when the person faces the user.

Based on the above, in this embodiment, the likelihood classifier 614 assigns a higher weight to a smaller relative depth, a smaller included angle and a smaller angle by which the identified human face object 401 turns in the image 40. The likelihood classifier 614 then determines the likelihood classification for each of the identified human face objects 401. In this embodiment, each of the identified human face objects 401 may be classified into one of a high likelihood classification, a medium likelihood classification, and a low likelihood classification.

In this embodiment, after each of the identified human face objects 401 has been classified by the likelihood classifier 614, the lip movement detection unit 615 is configured to detect, for each of the identified human face objects 401 classified into the high likelihood classification, presence or absence of a lip movement in the image 40. This is because detected lip movement of an identified human face object 401 further implies the act of speaking. The identified human face object 401 with detected lip movement is consequently deemed to be the target object.

In cases where none of the identified human face objects 401 is classified into the high likelihood classification, the lip movement detection unit 615 is configured to detect presence or absence of a lip movement of the identified human face objects 401 classified into the medium likelihood classification. In cases where none of the identified human face objects 401 is classified into either the high likelihood classification or the medium likelihood classification, the lip movement detection unit 615 is deactivated as none of the identified human face objects 401 captured in the image 40 is deemed to be a likely target speaker.

It is noted that in some embodiments, the lip movement detection unit 615 may be omitted. In such embodiments, the processor 6 selects one of the identified human face objects 401 as the target object. In some embodiments, the selected one of the identified human face objects 401 has the likelihood classification that indicates a relatively greater likelihood of the person corresponding thereto is a target speaker compared to other ones of the identified human face objects 401 in the image 40. In some embodiments, each of the identified human face objects 401 classified into the high likelihood classification is deemed to be the target object. The image analysis module 61 then transmits a signal indicating the identified human face objects 401 that are deemed to be the target object to the sound processing module 62.

The sound processing module 62 is configured to receive and process the sound information collected by the sound pickup module 5. For example, the sound processing module 62 may be configured to subject the sound information to analog-to-digital conversion, noise reduction processing, etc. In this embodiment, the sound processing module 62 includes a speech detection unit 621 and a sound processor 622.

The speech detection unit 621 is configured to detect speech content in the sound information collected by the sound pickup module 5. Detection of the speech content in the sound information indicates the presence of people speaking in the surrounding environment of the hearing aid system 2. In this embodiment, the image capturing module 4 is enabled to capture the image 40 only after the speech detection unit 621 transmits a signal indicating detection of the speech content.

The sound processor 622 is configured to perform a directional signal processing operation on the sound information so as to generate an output audio signal. That is, the directional signal processing operation retains sound that comes from areas corresponding to locations of the target objects in the image 40, and filters out sound that comes from other directions. In this embodiment, the directional signal processing operation is a beamforming operation.

Accordingly, the output audio signal contains an extracted voice signal that comes from an area corresponding to a location of a target object in the image 40 captured by the image capturing module 4. The sound processor 622 may further perform noise reduction and/or amplification on the extracted voice signal before transmitting the extracted voice signal to the audio output device 7. In this embodiment, the audio output device 7 is in the form of a pair of earphones connected respectively to the left and right side supports 32, and is coupled to the processor 6 for receiving and outputting the extracted voice signal. As such, a user wearing the hearing aid system 2 of this invention is able to hear the sound signal coming from the target speaker(s).

In one embodiment, the processor 6 may further include a communication unit 9 to communicate with an external electronic device 8 (See FIG. 2). In this embodiment, the communication unit 9 is configured to communicate with the external electronic device 8 using one of Wi-Fi, Zigbee, Bluetooth and near field communication (NFC).

The external electronic device 8 may be implemented using a mobile device, a tablet computer, a notebook computer, or the like. The external electronic device 8 includes a control unit (not shown in the drawings), a touch display 81 and a communication unit 82. The communication unit 82 may be implemented using an application program installed in the external electronic device 8.

When it is intended for the hearing aid system 2 to communicate with the external electronic device 8, a user may operate the touch display 81 to input a command that controls the communication unit 82 to attempt to establish a communication channel between the hearing aid system 2 and the external electronic device 8. After the communication channel is established, the processor 6 of the hearing aid system 2 transmits the image 40 captured by the image capturing module 4 to the external electronic device 8 via the communication unit 9.

The control unit of the external electronic device 8 then controls the touch display 81 to display the image 40 including the human face objects 401, and allows selection of one of the human face objects 401 as the target object. Afterward, the external electronic device 8 generates an external control signal indicating the location of the target object in the image 40, and transmits the external control signal to the hearing aid system 2 via the communication unit 82. Upon receipt of the external control signal, the image analysis module 61 bypasses the above operation related to selecting the target object from the identified human face objects 401, and operations of the sound processing module 62 proceed based on the external control signal.

It should be readily appreciated by those skilled in the art that the wearable accessory 3 further includes mechanisms for providing electric power to the electronic components mounted thereon, such as a battery (not shown in the drawings). Furthermore, the wearable accessory 3 may include a physical switch that allows the user to activate or deactivate the hearing aid system 2.

Figure 3:
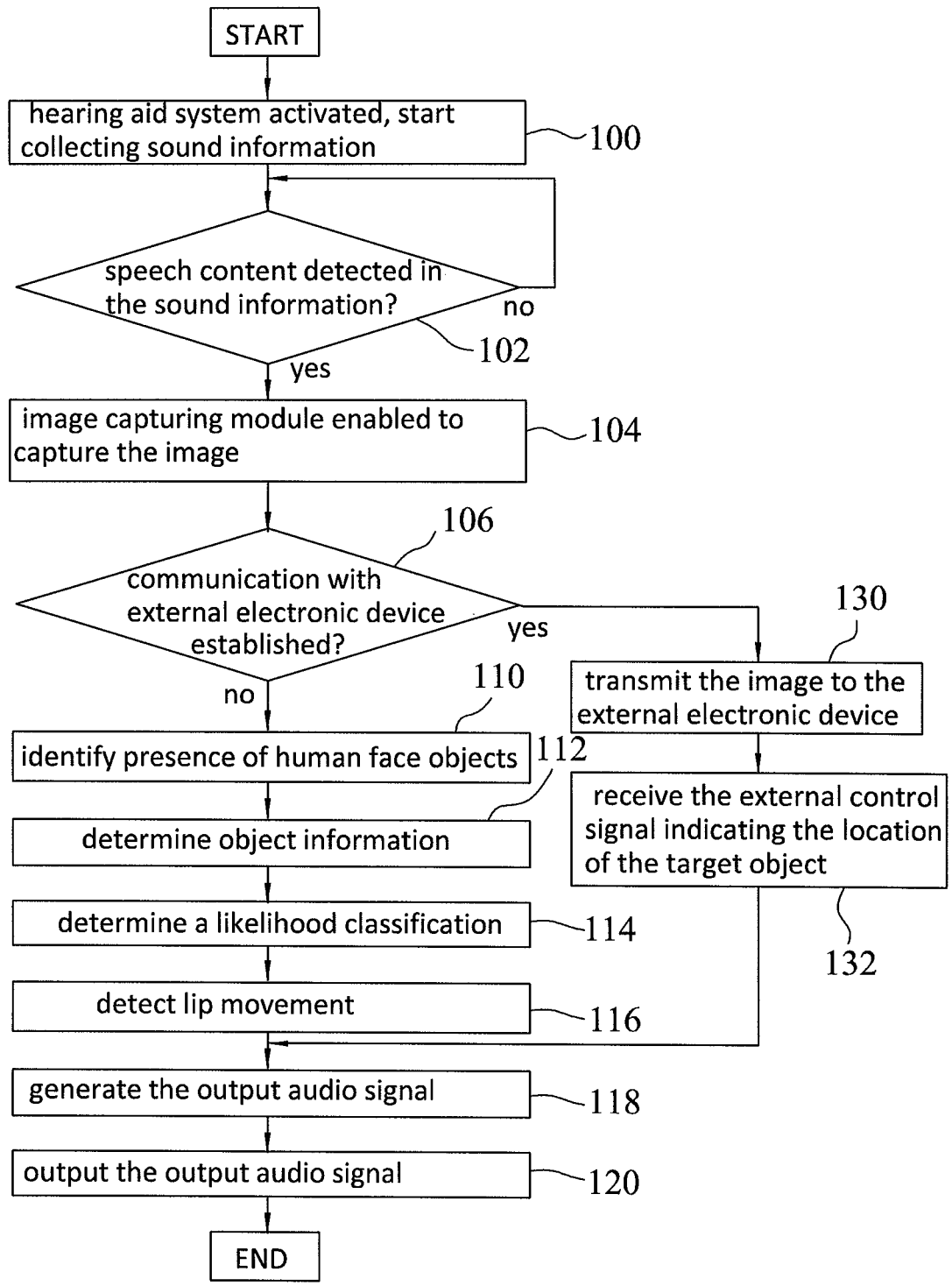
FIG. 3 is a flow chart of an embodiment of a method of audio signal processing, according to the present invention.

The hearing aid system 2 as described above and illustrated in FIGS. 1 and 2 are configured to execute an embodiment of a method of audio signal processing according to this invention, as shown in FIG. 3.

In step 100, the hearing aid system 2 is activated. This may be done after a user wears the wearable accessory 3 (in the form of a pair of eyeglasses in this embodiment). The sound pickup module 5 will start collecting sound information upon activation.

In step 102, the speech detection unit 621 continuously detects for speech content in the sound information collected by the sound pickup module 5. When the sound information is detected, the flow proceeds to step 104.

In step 104, the image capturing module 4 is enabled to capture the image 40.

In step 106, the processor 6 determines whether the communication channel between the hearing aid system 2 and the external electronic device 8 has been established. In the case that the hearing aid system 2 is not in communication with the external electronic device 8, the hearing aid system 2 operates in a first mode, and the flow proceeds to step 110. Otherwise, the hearing aid system 2 operates in a second mode, and the flow proceeds to step 130.

When operated in the first mode, in step 110, the image analysis module 61 identifies presence of human face objects 401 in the image 40 captured by the image capturing module 4.

In step 112, the image analysis module 61 is configured to determine object information corresponding respectively to the identified human face objects 401. That is, the depth analysis unit 611 determines the relative depth of each of the identified human face objects 401 in the image 40 relative to the hearing aid system 2. The angle analysis unit 612 determines the included angles between the reference axis 402 in the image 40 and the locations of the corresponding identified human face objects 401 in the image 40 (see FIG. 5). The turn analysis unit 613 determines the angle by which each of the identified human face objects 401 is turned in the image 40.

In step 114, the likelihood classifier 614 is configured to determine a likelihood classification for each of the identified human face objects 401, based on the object information.

In step 116, the lip movement detection unit 615 detects, for each of the identified human face objects 401 classified into the high likelihood classification (or the medium likelihood classification in the case that none of the identified human face objects 401 is classified into the high likelihood classification), presence or absence of lip movement. The identified human face object(s) 401 with detected lip movement is/are then selected as the target object(s).

In step 118, the sound processor 622 performs a beamforming operation on the sound information so as to generate the output audio signal that contains the extracted voice signal coming from the area corresponding to a location of the target object in the image 40.

In step 120, the output audio signal is transmitted to the audio output device 7 and outputted.

On the other hand, when operated in the second mode (i.e., the hearing aid system 2 is in communication with the external electronic device 8), in step 130, the processor 6 transmits the image 40 to the external electronic device 8 via the communication unit 9. As a result, the user of the hearing aid system 2 may manually select one or more of the identified human face objects 401 as the target object(s).

In step 132, the processor 6 receives the external control signal from the external electronic device 8, the external control signal indicating the location of the target object in the image 40 (selected by the user). The flow then goes to step 118.

It is noted that, while the use of the lip movement detection unit 615 may significantly increase accuracy of the target object selection, in the cases where it is preferable not to accidentally "filter out" voices from some particular objects, the lip movement detection unit 615 may be deactivated.

Accordingly, the identified human face objects 401 with the high likelihood classification are deemed to be the target objects. In cases where none of the identified human face objects 401 with the high likelihood classification is present, the identified human face objects 401 with the medium likelihood classification are deemed to be the target objects. In cases where none of the identified human face objects 401 with the high likelihood classification or the medium likelihood classification is present, the sound processor 622 may simply extract sound information in a front direction. In some embodiments, the turn analysis unit 613 may be omitted from the hearing aid system 2, and operations thereof may be omitted in the method as well.

In some embodiments, the image capturing module 4 may be mounted at other sections of the wearable accessory 3.

To sum up, the hearing aid system 2 of this invention provides two different ways for selecting the target speaker from captured image 40. In the first mode, the image analysis module 61 automatically performs the selecting operation based on object information. In the second mode, the target speaker is selected by the user. Accordingly, when the hearing aid system 2 of this invention is in use, the user is able to localize one or more target speakers in a noisy environment with multiple speakers.

While the present invention has been described in connection with what are considered the most practical embodiments, it is understood that this invention is not limited to the disclosed embodiments but is intended to cover various arrangements included within the spirit and scope of the broadest interpretation so as to encompass all such modifications and equivalent arrangements.

What is claimed is:

1. A method of audio signal processing to be implemented by a hearing aid system, the hearing aid system including an image capturing module, a sound pickup module, and a processor, said method comprising:
   (a) collecting, using the sound pickup module, sound information of a surrounding environment of the hearing aid system;
   (b) capturing, using the image capturing module, an image of the surrounding environment of the hearing aid system;
   (c) using the processor to perform a directional signal processing operation on the sound information collected by the sound pickup module so as to generate an output audio signal, the output audio signal containing an extracted voice signal that comes from an area corresponding to a location of a target object in the image captured by the image capturing module; and
   (d) outputting the output audio signal;
   wherein step (c) includes the following sub-steps of:
      (c1) identifying, using the processor, presence of human face objects in the image captured by the image capturing module;
      (c2) determining, using the processor, object information corresponding respectively to the identified human face objects;
      (c3) determining, using the processor, a likelihood classification for each of the identified human face objects based on the object information corresponding thereto,
   wherein, for each of the identified human face objects, the likelihood classification is related to a likelihood of a person corresponding to the identified human face object being a target speaker; and
      (c4) selecting, using the processor, one of the identified human face objects as the target object, the selected one of the identified human face objects having the likelihood classification that indicates a relatively greater likelihood of the person corresponding thereto is a target speaker compared to other ones of the identified human face objects in the image.

2. The method of claim 1, wherein, in sub-step (c2), the object information for each of the identified human face objects includes at least one of the following:
   a relative depth of the identified human face object in the image relative to the hearing aid system;

an included angle formed between a reference axis in the image and the location of the identified human face object in the image, the reference axis representing an axis of the image capturing module; and an angle by which the corresponding identified human face object is turned in the image.

3. The method of claim 1, wherein, in sub-step (c2), the object information includes relative depth information and relative orientation information for the corresponding identified human face object relative to the hearing aid system, different relative depths are pre-assigned with different weights, different relative orientations are pre-assigned with different weights, and the likelihood classification for each of the identified human face objects is determined with reference to the weights corresponding to the relative depth information and the relative orientation information of the respective object information.

4. The method of claim 3, wherein the relative orientation information indicates an included angle formed between a reference axis in the image and the location of the corresponding identified human face object in the image, the reference axis representing an axis of the image capturing module.

5. The method of claim 3, wherein the relative orientation information indicates an angle by which the corresponding identified human face object is turned in the image.

6. The method of claim 1, wherein a plurality of the images are captured in step (b), and the object information determined in sub-step (c2) includes an indication of presence or absence of lip movement of the corresponding identified human face object in the images.

7. The method of claim 2, wherein a plurality of the images are captured in step (b), and the object information determined in sub-step (c2) includes an indication of presence or absence of lip movement of the corresponding identified human face object in the images.

8. The method of claim 1, wherein step (c) includes the following sub-steps of:
transmitting, using the processor, the image captured by the image capturing module to an external electronic device; and
receiving, by the processor, an external control signal from the external electronic device, the external control signal indicating the location of the target object in the image.

9. A method of audio signal processing to be implemented by a hearing aid system, the hearing aid system including an image capturing module, a sound pickup module, and a processor, said method comprising:
(a) collecting, using the sound pickup module, sound information of a surrounding environment of the hearing aid system;
(b) capturing, using the image capturing module, an image of the surrounding environment of the hearing aid system;
(c) using the processor to perform a directional signal processing operation on the sound information collected by the sound pickup module so as to generate an output audio signal, the output audio signal containing an extracted voice signal that comes from an area corresponding to a location of a target object in the image captured by the image capturing module; and
(d) outputting the output audio signal;
wherein step (c) includes the sub-step of operating the processor in a selected one of a first mode and a second mode;
wherein, in the first mode, the processor is configured to:

identify presence of human face objects in the image captured by the image capturing module;
determine object information corresponding respectively to the identified human face objects;
determine a likelihood classification for each of the identified human face objects based on the object information corresponding thereto,
wherein, for each of the identified human face objects, the likelihood classification is related to a likelihood of a person corresponding to the identified human face object being a target speaker; and
select at least one of the identified human face objects as the target object, the selected one of the identified human face objects having the likelihood classification that indicates a relatively greater likelihood of the person corresponding thereto is a target speaker compared to other ones of the identified human face objects in the image; and
wherein, in the second mode, the processor is configured to:
transmit the image captured by the image capturing module to an external electronic device; and
receive an external control signal from the external electronic device, the external control signal indicating the location of the target object in the image.

10. The method of claim 1, wherein, in step (b), the image capturing module is enabled to capture the image only after detection by the processor that the sound information collected by the sound pickup module includes speech content.

11. The method of claim 1, wherein, in step (c), the directional signal processing operation is a beamforming operation.

12. The method of claim 1, wherein, in step (d), the output audio signal is transmitted by the processor to an audio output device coupled thereto.

13. A hearing aid system comprising:
a sound pickup module for collecting sound information of a surrounding environment of the hearing aid system;
an image capturing module for capturing an image of the surrounding environment of the hearing aid system;
a processor coupled to said sound pickup module and said image capturing module, said processor including a sound processing module that performs a directional signal processing operation on the sound information collected by said sound pickup module so as to generate an output audio signal, the output audio signal containing an extracted voice signal that comes from an area corresponding to a location of a target object in the image captured by said image capturing module; and
an audio output device coupled to said processor for outputting the output audio signal;
wherein said processor further includes:
an image analysis module configured to identify presence of human face objects in the image captured by said image capturing module, to determine object information corresponding respectively to the identified human face objects, and to determine a likelihood classification for each of the identified human face objects based on the object information corresponding thereto;
wherein, for each of the identified human face objects, the likelihood classification is related to a likelihood of a person corresponding to the identified human face object being a target speaker; and said sound processing module is configured to select at least one of the identified human face objects as the target object, the selected one of the identified human face objects having the likelihood classification that indicates a relatively greater likelihood of the person corresponding thereto is a target speaker compared to other ones of the identified human face objects in the image.

14. The hearing aid system of claim 13, wherein said image analysis module includes at least one of:
a depth analysis unit for determining a relative depth of each of the identified human face objects in the image relative to the hearing aid system;
an angle analysis unit for determining included angles each formed between a reference axis in the image and the location of a corresponding one of the identified human face objects in the image, the reference axis representing an axis of said image capturing module; and
a turn analysis unit for determining an angle by which each of the identified human face objects is turned in the image.

15. The hearing aid system of claim 13, wherein the object information determined by said image analysis module includes relative depth information and relative orientation information for the corresponding identified human face object relative to the hearing aid system, different relative depths are pre-assigned with different weights in said processor, different relative orientations are pre-assigned with different weights in said processor, and said image analysis module includes a likelihood classifier that determines the likelihood classification for each of the identified human face objects with reference to the weights corresponding to the relative depth information and the relative orientation information of the respective object information.

16. The hearing aid system of claim 15, wherein the relative orientation information indicates an included angle formed between a reference axis in the image and the location of the corresponding identified human face object in the image, the reference axis representing an axis of said image capturing module.

17. The hearing aid system of claim 15, wherein the relative orientation information indicates an angle by which the corresponding identified human face object is turned in the image.

18. The hearing aid system of claim 13, wherein said image capturing module is configured to capture a plurality of the images, and said image analysis module includes a lip movement detection unit, the object information determined by said image analysis module including an indication of presence or absence of lip movement of the corresponding identified human face object in the images as detected by said lip movement detection unit.

19. The hearing aid system of claim 14, wherein said image capturing module is configured to capture a plurality of the images, and said image analysis module includes a lip movement detection unit, the object information determined by said image analysis module including an indication of presence or absence of lip movement of the corresponding identified human face object in the images as detected by said lip movement detection unit.

20. The hearing aid system of claim 13, wherein said processor includes a communication unit configured to:
transmit the image captured by said image capturing module to an external electronic device; and
receive an external control signal from the external electronic device, the external control signal indicating the location of the target object in the image.

21. The hearing aid system of claim 20, wherein said communication unit is configured to communicate with the external electronic device using one of Wi-Fi, Zigbee, Bluetooth and near field communication.

22. A hearing aid system comprising:
a sound pickup module for collecting sound information of a surrounding environment of the hearing aid system;
an image capturing module for capturing an image of the surrounding environment of the hearing aid system;
a processor coupled to said sound pickup module and said image capturing module, said processor including a sound processing module that performs a directional signal processing operation on the sound information collected by said sound pickup module so as to generate an output audio signal, the output audio signal containing an extracted voice signal that comes from an area corresponding to a location of a target object in the image captured by said image capturing module; and
an audio output device coupled to said processor for outputting the output audio signal;
wherein said processor is operable in a selected one of a first mode and a second mode;
wherein, in the first mode, said processor is configured to:
identify presence of human face objects in the image captured by said image capturing module;
determine object information corresponding respectively to the identified human face objects;
determine a likelihood classification for each of the identified human face objects based on the object information corresponding thereto,
wherein, for each of the identified human face objects, the likelihood classification is related to a likelihood of a person corresponding to the identified human face object being a target speaker; and
select at least one of the identified human face objects as the target object, the selected one of the identified human face objects having the likelihood classification that indicates a relatively greater likelihood of the person corresponding thereto is a target speaker compared to other ones of the identified human face objects in the image; and
wherein, in the second mode, said processor is configured to:
transmit the image captured by said image capturing module to an external electronic device; and
receive an external control signal from the external electronic device, the external control signal indicating the location of the target object in the image.

23. The hearing aid system of claim 13, wherein said sound processing module includes a speech detection unit, and said image capturing module is enabled by said processor to capture the image only after detection by said speech detection unit that the sound infotijiation collected by said sound pickup module includes speech content.

24. The hearing aid system of claim 13, wherein the directional signal processing operation is a beamforming operation.

25. The hearing aid system of claim 13, further comprising a wearable accessory on which said image capturing module, said sound pickup module and said processor are mounted.

26. The hearing aid system of claim 25, wherein said wearable accessory includes a front frame part on which said image capturing module is disposed, and left and right side supports respectively connected to left and right sides of said front frame part.

27. The hearing aid system of claim 26, wherein said sound pickup module is a microphone array including a plurality of microphones, each of said microphones being disposed on one of said front frame part and said left and right side supports.

28. The hearing aid system of claim 26, wherein said processor is mounted at one of said left and right side supports.

29. The hearing aid system of claim 26, wherein said audio output device includes a pair of earphones connected respectively to said left and right side supports.

30. The hearing aid system of claim 26, wherein said wearable accessory is an eyeglass frame having a lens frame serving as said front frame part, and a pair of temples serving as said left and right side supports.

* * * * *